(12) United States Patent
Hirao et al.

(10) Patent No.: US 7,435,859 B2
(45) Date of Patent: Oct. 14, 2008

(54) SUMANENE AND METHOD FOR MANUFACTURING THE SAME

(75) Inventors: Toshikazu Hirao, Suita (JP); Hidehiro Sakurai, Okazaki (JP); Taro Daiko, Nishitokyo (JP)

(73) Assignee: Kaneka Corporation, Osaka (JP)

( * ) Notice: Subject to any disclaimer, the term of this patent is extended or adjusted under 35 U.S.C. 154(b) by 149 days.

(21) Appl. No.: 10/543,549

(22) PCT Filed: Jan. 27, 2004

(86) PCT No.: PCT/JP2004/000678

§ 371 (c)(1),
(2), (4) Date: Jul. 27, 2005

(87) PCT Pub. No.: WO2004/067446

PCT Pub. Date: Aug. 12, 2004

(65) Prior Publication Data

US 2006/0142370 A1    Jun. 29, 2006

(30) Foreign Application Priority Data

Jan. 31, 2003    (JP) .............................. 2003-024462

(51) Int. Cl.
*C07C 13/62* (2006.01)
(52) U.S. Cl. ........................ 585/27; 977/734
(58) Field of Classification Search ............ 585/27; 977/734
See application file for complete search history.

(56) References Cited

FOREIGN PATENT DOCUMENTS

JP    2000077186 A  *  3/2000

OTHER PUBLICATIONS

Sastry et al, J. Chem. Soc., Perkin Trans. 2, 2001, 30-40.*
Sakurai et al. (Science, 2003, v. 301, p. 1878).*
JPO translation of claims for JP 3899698 B obtained on Aug. 2, 2007.*
Derwent abstract of JP 2000077186 A.*
Robert W. Murray, "The Mechanism of Ozonolysis", Bell Telephone Laboratories, Inc., Murray Hill, New Jersey, Oct. 1968. (book).
John E. McMurry, "Organiz Chemistry of Low-Valent Titanium", *Accounts of Chemical Research*, vol. 7, No. 9, Sep. 1974, pp. 281-286.
John E. McMurry, "Titanium-Induced Dicarbonyl-Coupling Reactions", *Acc. Chem. Res.*, 1983, Vo. 16, pp. 405-411.
McMurry et al., "Systhesis of Cycloalkenes by Intramolecular Titanium-Induced Dicarbonyl Coupling", *J. Org. Chem.*, vol. 42, No. 15, 1977, pp. 2655-2656.
Clive et al., "Total Synthesis of Both (+)- Compactin and (+)- Mevinolin. A General Stragety Based on the Use of a Special TiCl3/C8K Mixture for Dicarbonyl Coupling", *J. Am. Chem. Soc.*, 1988, vol. 110, pp. 6914-6916.

Sakurai et al., "A Synthesis of Sumanene, a Fullerene Fragment", *Science*, Sep. 26, 2003, col. 301, pp. 1878.

(Continued)

*Primary Examiner*—Kamal Saeed
*Assistant Examiner*—Robert Havlin
(74) *Attorney, Agent, or Firm*—Hamre, Schumann, Mueller & Larson, P.C.

(57) ABSTRACT

The present invention provides Sumanene, its derivative and a method for manufacturing Sumanene and its derivative. As shown by a below-described scheme, benzotris(norbornadiene) (a below formula (87)) is firstly synthesized from norbornadiene (a below formula (86)). Then, the compound is subjected to a metathesis reaction so as to synthesize hexahydrosumanene (a below formula (88)), and it is dehydrogenized so as to obtain Sumanene (a below formula (84)). Thereby, Sumanene can be mass-synthesized under a moderate condition. In addition, a compound with a structure where a benzyl position of Sumanene is substituted by a N atom or an O atom can be obtained similarly, and various derivatives also can be obtained by further chemical modification of the compound. Sumanene and its derivative are suitable for electronic materials, synthesis raw materials for various kinds of fullerenes and heterofullerenes, and the like.

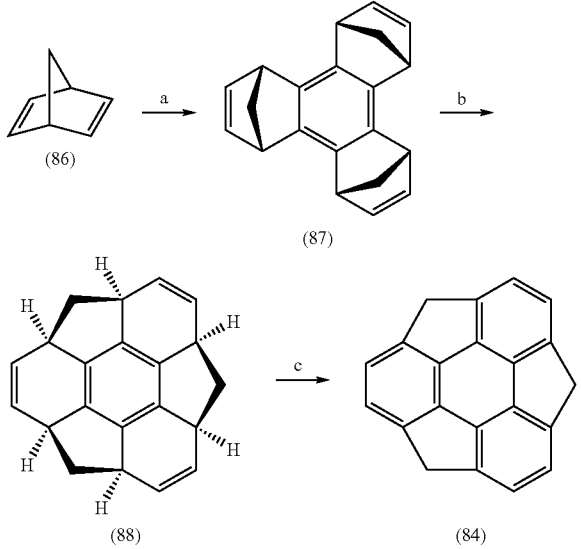

Scheme 1

Condition of the Reaction
a) BuLi, t-BuOK, BrCH$_2$CH$_2$Br, THF, −78° C. to −45° C. subsequently CuI, a room temperature
b) catalyst quantity of (PCy$_3$)$_2$RuCl$_2$═CHPh, CH$_2$═CH$_2$, toluene, 0° C. to 80° C.
c) DDQ, toluene, 110° C.

5 Claims, 3 Drawing Sheets

OTHER PUBLICATIONS

Manaa et al., "Prediction of Extended Aromaticity for a Novel $C_{48}N_{12}$ Azafullerene Structure", *J. Am. Chem. Soc.*, 2002, vol. 124, pp. 13990-13991.

Hummelen et al., "Isolation of the Heterofullerene $C_{59}N$ as its Dimer $(C_{59}N)$", *Science* Sep. 15, 1995, vol. 269, pp. 1554-1556.

Sygula et al., "A Practical, Large Scale Synthesis fo the Corannulene System", *J. Am. Chem. Soc.*, 2000, vol. 122, pp. 6323-6324.

Priyakumar et al., "First an Initio and Density Functional Study on the Structure, Bowl-to-Bowl Inversion Barrier, and Vibrational Spectra of the Elusive $C_{3U}$-Symmetric Buckybowl: Sumanene, $C_{12}H_{12}$", *J. Phys. Chem A*, 2001, vol. 105, pp. 4488-4494.

Priyakumar et al., "Theory provides a clue to accomplish the synthesis of sumanene, $C_{12}H12$, the prototypical $C_{3v}$-buckybowl", *Tetrahedron Letters*, vol. 42, 2001, pp. 1379-1381.

Imamura et al., "Triphenyleno[1, 12-*bcd*: 4, 5-*b'c'd'*:8, 9-b"c"d"] trithiophene: the first bowl-0shaped heteraromatic", *Chem. Commun.*, 1999, pp. 1859-1860.

Greene et al., "Protective Groups in Organic Systhesis", *J. Org. Chem.*, 2002, vol. 67, pp. 7894-7897.

Hart et al., "Iptycenes: Extended Triptycenes", *Tetrahedron*, 1986, Vo. 42, No. 6, pp. 1641-1654.

Hart et al., *Tetrahedron*, 1987, vol. 43, No. 22, pp. 5203-5224.

Raymo et al., "The Regioselective Generation of Arynes from Polyhalogenobenzenes. An Improved Synthesis of *syn*- and *anti*- 1, 4, 5, 8, 9 12-Hexahydro- 1, 4:5, 8:9, 12- triepoxytriphenylene", *Tetrahedron*, vol. 48, No. 33, pp. 6827-6838.

Philip S. Bailey, "The Reactions of Ozone with Organic Compounds", Department of Chemistry, The University of Texas, Austin Texas, Sep. 14, 1957. (book).

* cited by examiner

SUMANENE AND METHOD FOR MANUFACTURING THE SAME

TECHNICAL FIELD

The present invention relates to Sumanene and a method for manufacturing the same.

BACKGROUND ART

A group of carbon homologues that include various kinds of fullerenes such as $C_{60}$ (a below formula (82)) and $C_{70}$, and carbon nanotubes (hereinafter, they may be generically called "fullerenes") are of interest as next-generation materials because of their specific properties. Fullerenes with various structures are known besides $C_{60}$ and $C_{70}$, which respectively have inherent properties. World-wide research has been keenly conducted to add various functions further to fullerenes by chemical modification.

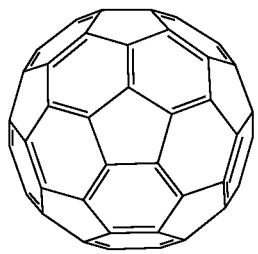

(82)

However, at present, since a method for manufacturing fullerenes is limited to a so-called arc discharge method and the like, $C_{60}$ and $C_{70}$ can be obtained relatively easily, but other fullerenes can be produced only in small amounts, and are very difficult to obtain. Therefore, such poor kind variations of starting raw materials causes a difficulty in manufacturing high-functional materials with various structures by modifying fullerenes chemically.

In the light of the above-described problem, attempts for chemical syntheses of fullerenes are made keenly all over the world, but this research has just started, and no one has accomplished it yet. However, molecular structures of products can be controlled freely by a method of organic synthetic chemistry, unlike by the arc discharge method, and therefore, if the research proceeds, fullerenes, which are conventionally difficult to obtain, are expected to be obtained freely. Moreover, it is considered that, if not only the existing fullerenes but also new fullerenes and their derivatives can be synthesized, the possibilities of designing new materials will be highly enhanced. For example, heterofullerenes that are obtained by substituting hetero atoms for some of carbon atoms of fullerenes are focused on in a theoretical research (see, for example, "M. Riad Manaa, David W. Sprehn, and Heather A. Ichord, J. Am. Chem. Soc., 2002, 124, p. 13990-13991."). However, since such heterofullerenes, except only a few kinds of compounds such as $C_{59}N$ (see "Science, 1995, 269, p. 1554."), have not manufactured yet, establishment of the methods for their synthesis in organic chemistry are sought.

At present, research for synthesizing a compound including a non-planar conjugated carbon skeleton that is a partial structure of $C_{60}$ has proceeded. However, so far, it has been reported only that a compound called Corannulene (a below formula (83)) and its derivative were synthesized in 1966, and the synthesis has been conducted still at a laboratory level.

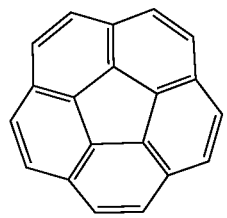

(83)

Corannulene is a compound that is synthesized as the first compound including the partial structure of $C_{60}$ in the world, thus having an academic significance. In addition, a route for manufacturing a relatively large amount of Corannulene under moderate conditions in a flask has been reported as well (Andrzej Sygula and Peter W. Rabideau, J. Am. Chem. Soc., 2000, 122, p. 6323-6324.). However, there would be a problem if Corannulene is used as a synthesis raw material or the like for fullerenes. The reason for this is because, since all of the carbon atoms in the skeleton of Corannulene are taken into a benzene nucleus, reactivity thereof is not very high. Therefore, derivatives of Corannulene with only limited structures are synthesized at present, and thus it is expected to be difficult to lead these derivatives further to the compounds such as $C_{60}$.

DISCLOSURE OF INVENTION

Accordingly, it is an object of the present invention to provide a compound that can be used as a synthesis raw material or the like for fullerenes and heterofullerenes, and a method for manufacturing the same.

In order to solve the above-mentioned object, the present invention provides a compound represented by a below-described general formula (1), a tautomer of the compound, a stereoisomer of the compound, or a salt of any of the compound, the tautomer and the stereoisomer.

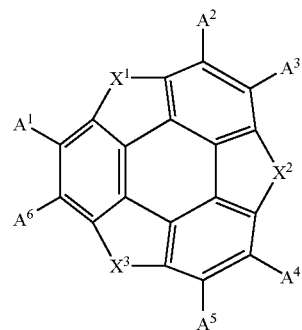

(1)

Here, in the formula, $A^1$ to $A^6$ are the same or different, and each of the $A^1$ to $A^6$ is a hydrogen atom, a straight or branched alkyl group or an aromatic hydrocarbon group, in a case where a hydrogen atom at a benzyl position exists on any of the $A^1$ to $A^6$, the hydrogen atom may be substituted by a substituent.

The substituents on the $A^1$ to $A^6$ are the same or different, and each of the substituents is a halogen, a low molecular-weight or a polymer chain that is straight or branched (a principal chain (main chain) and a side chain of the low molecular-weight or the polymer chain may or may not include a hetero atom, may or may not include an unsaturated bond, and may or may not include a cyclic structure), a carbocyclic ring or a heterocyclic ring (the ring may be a monocyclic ring or a condensed ring, may be saturated or unsaturated, and may or may not include a substituent), an electron-releasing group or an electron-withdrawing group. Alternatively, the substituents bonded to the same $A^r$ (r is any one of integers from 1 to 6) may be bonded to each other via a covalent bond so as to form a carbocyclic ring or a heterocyclic ring with the $A^r$ to which the substituents are bonded (the ring may be a monocyclic ring or a condensed ring, may be saturated or unsaturated, and may or may not include a substituent).

$X^1$ to $X^3$ are the same or different, and each of the $X^1$ to $X^3$ may be a methylene group (a below formula (2)), a vinylidene group (a below formula (3)), a carbonyl group (a below formula (4)), a thiocarbonyl group (a below formula (5)), an iminomethylene group (a below formula (6)), an imino group (a below formula (7)) or an oxygen atom (a below formula (8)). In a case where an hydrogen atom exists on any of the $X^1$ to $X^3$, the hydrogen atom may be substituted by a substituent.

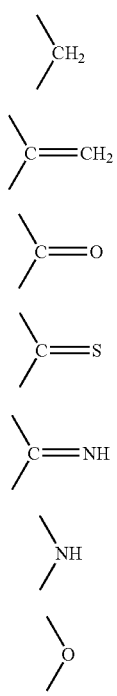

The substituents on the $X^1$ to $X^3$ are the same or different. Each of the substituents is a halogen, a low molecular-weight or a polymer chain that is straight or branched (a principal chain and a side chain of the low molecular-weight or the polymer chain may or may not include a hetero atom, may or may not include an unsaturated bond, and may or may not include a cyclic structure), a carbocyclic ring or a heterocyclic ring (the ring may be a monocyclic ring or a condensed ring, may be saturated or unsaturated, and may or may not include a substituent). An electron-releasing group or an electron-withdrawing group, alternatively, the substituents bonded to the same $X^a$ (a is any one of integers from 1 to 3) may be bonded to each other via a covalent bond so as to form a carbocyclic ring or a heterocyclic ring with the $X^a$ to which the substituents are bonded (the ring may be a monocyclic ring or a condensed ring, may be saturated or unsaturated, and may or may not include a substituent).

DESCRIPTION OF THE INVENTION

Figure 1:
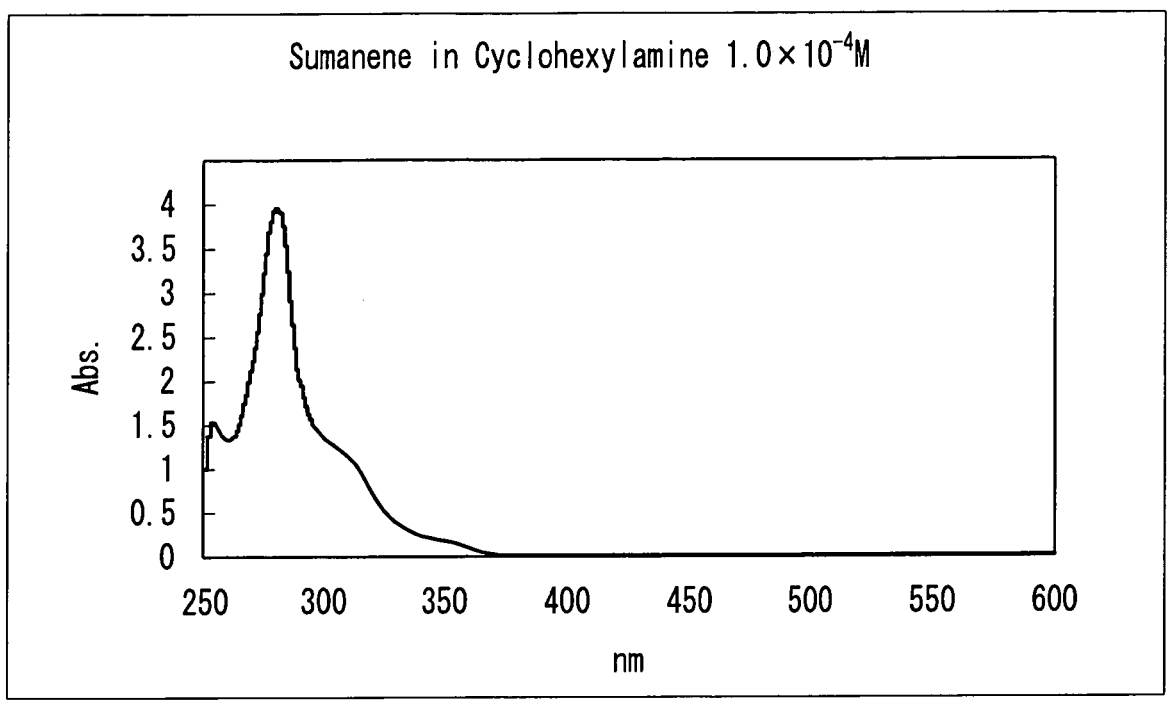
FIG. 1 is an UV-VIS spectrogram of Sumanene, where CHA is used as a solvent.

More specific description of the present invention will be provided below.

Another chemical structure that has been of interest besides Corannulene is a structure called Sumanene (a below formula (84)). Whereas Corannulene includes a $C_5$-symmetric-part skeleton of $C_{60}$, Sumanene includes a $C_3$-symmetric-part skeleton of $C_{60}$. In addition, unlike Corannulene, Sumanene has a significant feature of including carbons at three benzyl positions.

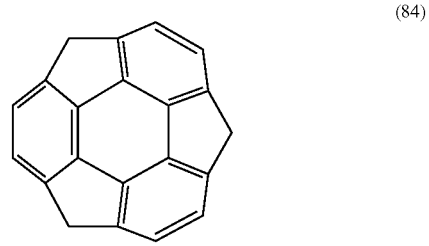

Generally, a compound including a carbon at a benzyl position has a high value as a synthesis raw material. The reason for this is because, since a carbon at a benzyl position has very high activity, and can generate various active species such as a cationic species, an anionic species and carbenes, such a compound including a carbon at a benzyl position can be applied to a further bond formation reaction after being converted into these active species. Accordingly, it is considered that, since Sumanene has a much higher reactivity than Corannulene, various functional groups can be introduced directly to Sumanene by, for example, an oxidation reaction or the like at a benzyl position so as to synthesize various derivatives thereof. Moreover, it is expected that various compounds besides fullerenes further can be synthesized by using these derivatives as raw materials.

In addition, the compound including a carbon at a benzyl position is advantageous as a synthesis raw material, and besides, the active species itself has a high utility value. For example, a benzyl anion species of Sumanene includes a structure similar to that of a cyclopentadienyl anion, and thus is considered to have a metal-clathration ability and the like. Accordingly, Sumanene itself has wide industrial applicability, and besides, its development as a compound for a model research on a metal-inclusion type fullerene compound and the like also can be expected.

As mentioned above, since Sumanene has a great value in an academic field, and its value on the industrial applicability also is estimated to be high, many researchers have been worked toward the synthesis thereof. However, a successful synthesis of Sumanene has not been reported yet, which may be because of its high molecular distortion. Several documents refer to Sumanene, but they only provide theoretical calculations and the like (see, for example, "U. Deva Priyakumar and G. Narahari Sastry, J. Phys. Chem. A, 2001, 105, p. 4488-4494." and "U. Deva Priyakumar and G. Narahari Sastry, Tetrahedron Letters, 2001, 42, p. 1379-1381.").

In addition, a compound that is obtained by substituting sulfur atoms for carbons at benzyl positions of Sumanene (a below formula (85)) is synthesized (Koichi Imamura, Kazuo Takimiya, Yoshio Aso and Tetsuo Otsubo, Chem. Commun., 1999, p. 1859-1860.). This compound it self is interesting, but the synthesis thereof currently requires a strict condition including a temperature of 1000° C. in vacuum, and thus mass-production of the compound for industrial application is difficult. Furthermore, the properties of the compound are considerably different from those of Sumanene. For example, reactivity of the sulfur atom is not as high as that of a carbon at a benzyl position, and a degree of the reactivity is considered to be as low as an oxo group or the like can be added. As mentioned above, the chemical structure of Sumanene and the usability thereof can be expected, but there has been no example of its successful synthesis yet.

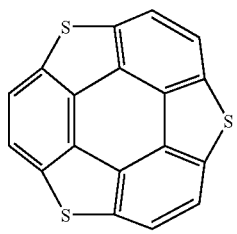

(85)

The inventors of the present invention have succeeded in the synthesis of Sumanene for the first time in the world. And they have established the compound of the present invention (that is, Sumanene and its derivative) represented by the above general formula (1), and a method for manufacturing the compound.

A method for manufacturing the compound represented by the general formula (1), a tautomer of the compound, a stereoisomer of the compound, or a salt of any of the compound, the tautomer and the stereoisomer is not limited particularly, and it may be manufactured by any methods, but preferably is manufactured by the below-described manufacturing method of the present invention. According to this manufacturing method, Sumanene and its derivative can be obtained without difficulty by using the methodology of organic synthetic chemistry. For example, Sumanene as a parent compound also can be synthesized in only three steps from easily-available and low-cost norbornadiene (a below formula (86)) under a moderate condition in a flask, as shown in a below Scheme 1.

Scheme 1

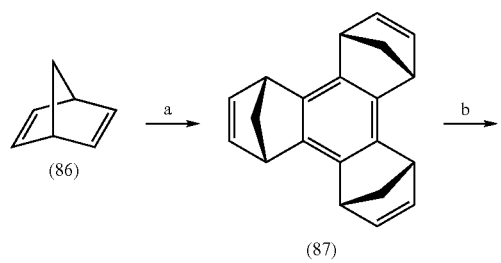

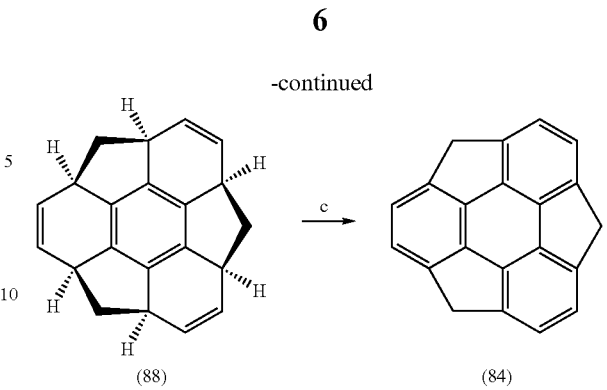

Condition of the Reaction
a) BuLi, t-BuOK, BrCH$_2$CH$_2$Br, THF, −78° C. to −45° C. subsequently CuI, room temperature
b) catalyst quantity of (PCy$_3$)$_2$RuCl$_2$=CHPh, CH$_2$=CH$_2$, toluene, 0° C. to 80° C.
c) DDQ, toluene, 110° C.

The manufacturing method of the present invention will be described below more specifically. That is, firstly, a compound represented by a below formula (76) is prepared. This compound and its salt are the new compounds according to the invention by the present inventors, and can be converted into Sumanene and its derivative via an oxidation (dehydrogenation) reaction.

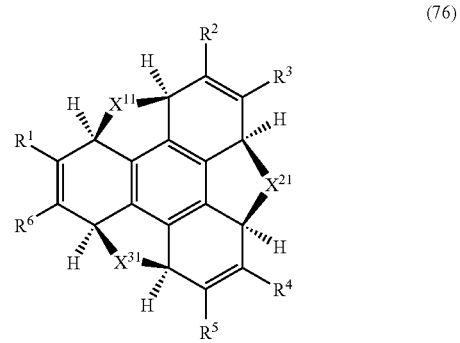

(76)

Here, in the formula, R$^1$ to R$^6$ are the same or different, and each of them may be a hydrogen atom, a straight or branched alkyl group or an aromatic hydrocarbon group, and preferably is a hydrogen atom, a straight or branched alkyl group with the carbon number of 1 to 6, a phenyl group or a naphthyl group. In addition, X$^{11}$, X$^{21}$ and X$^{31}$ are the same or different, and each of them may be a methylene group, an imino group or an oxygen atom. In the case where any of the X$^{11}$, X$^{21}$ and X$^{31}$ is an imino group, a hydrogen atom in the imino group may be substituted by a protecting group. A method for manufacturing this compound will be described below.

A method for manufacturing the compound represented by the formula (76) and its salt is not limited particularly, but preferably is a manufacturing method including a metathesis reaction of the compound represented by a below formula (77). This method is the new manufacturing method according to the invention by the present inventors. The metathesis reaction is a well-known reaction, but the present inventors have found how to apply this reaction to producing the compound represented by the below formula (77). By virtue of the invention of this method, Sumanene and its derivative can be obtained without difficulty.

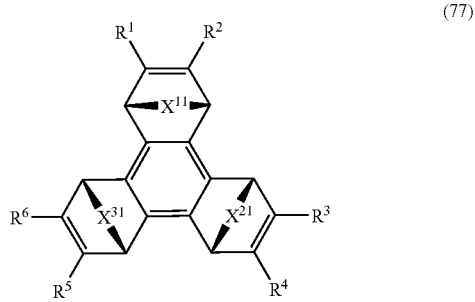

(77)

Here, $R^1$ to $R^6$, $X^{11}$, $X^{21}$ and $X^{31}$ in the formula are the same as the $R^1$ to $R^6$, $X^{11}$, $X^{21}$ and $X^{31}$ in the formula (76), respectively.

A condition of the metathesis reaction is not limited particularly, and the metathesis reaction can be caused similarly to a conventional metathesis reaction, but preferably by using a catalyst. The catalyst is not limited particularly, and catalysts that are usually used as so-called metathesis catalysts may be used, which may be used alone or in combination of two kinds or more. In addition, the catalyst preferably includes, for example, at least one element selected from the group consisting of ruthenium, aluminum, titanium, molybdenum and tungsten. Various kinds of such metathesis catalysts, in particular, catalysts including ruthenium or molybdenum have been exploited. Specifically, it is particularly preferable that the catalyst used in the present invention includes, for example, at least one selected from the group consisting of $(PCy_3)_2RuCl_2$=CHPh, that is, bis(tricyclohexylphosphino)benzylidene ruthenium (II) chloride, $Al(C_2H_5)_3$—$TiCl_4$, $Al(C_2H_5)_3$—$MoCl_3$ and $Al(C_2H_5)_3$—$WCl_6$, but it is not limited to these. An amount of the catalyst to be used also is not limited particularly, and may be adjusted as appropriate considering reaction efficiency, cost or the like, but preferably is, for example, a so-called stoichiometric amount or less. The appropriate amount of the catalyst to be used varies according to a kind of the catalyst, a reaction scale or the like, and it is, for example, approximately 5 mol % in a reaction at a flask-level, which is not constant though, with respect to an amount of the compound represented by the formula (77). Generally, in a catalytic reaction, when a reaction scale is larger, a relative amount of a catalyst to be used can be smaller (that is, a ratio of the amount of the catalyst to be used with respect to an amount of a substrate can be smaller).

Moreover, it is preferable that the metathesis reaction is caused by using one additional kind of olefin that reacts with the compound of the formula (77), in the light of reaction efficiency and a yield. The olefin in this case is not limited particularly in kind, but for example, ethylene is more preferable in the light of reaction efficiency, cost, handling simplicity and the like.

Examples of the procedures and reaction mechanism in the case of using the one additional kind of olefin, for example, ethylene will be described below. The compound of the formula (77) is firstly combined with ethylene by the metathesis reaction so as to open rings by cutting olefinic linkages in the compound of the formula (77). And then, the thus obtained reaction product is further subjected to the metathesis reaction so as to close rings, thereby obtaining the compound represented by the formula (76). According to this ring-closing reaction, ethylene is generated again, and finally is removed from the system. Thereby, the compound represented by the formula (76) can be obtained more efficiently.

Other materials to be used and reaction conditions in the metathesis reaction are not limited particularly, and can be set as appropriate with reference to the conventional metathesis reaction or the like. As a solvent, for example, aromatic hydrocarbon such as toluene and xylene, halides (halogen-containing solvents) such as dichloromethane, chloroform and dichloroethane, ether solvents such as diethylether, dimethoxyethane and tetrahydrofuran, highly-polar solvents such as acetonitrile and dimethyl sulfoxide and the like can be used. These solvents may be used alone or in combinations of two or more. Reaction temperatures and reaction time are not also limited particularly, and may be set as appropriate according to structures of the $R^1$ to $R^6$, $X^{11}$, $X^{21}$ and $X^{31}$ in the figure (77), a reaction scale or the like. In addition, methods for separation and purification of the reaction product are not limited particularly, and they may be conducted as appropriate using a known method such as column chromatography and GPC.

As mentioned above, the compound of the formula (76) can be manufactured from the compound of the formula (77). A method for manufacturing the compound represented by the formula (77) also is not limited particularly, but preferably is a manufacturing method including halogenating compounds represented by below formulae (78) to (80), and cyclizing the thus halogenated compounds by Wurtz-type coupling.

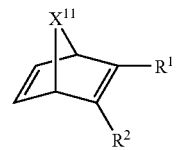

(78)

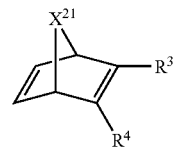

(79)

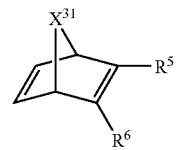

(80)

Here, $R^1$ to $R^6$, $X^{11}$, $X^{21}$ and $X^{31}$ in the formulae (78) to (80) are the same as the $R^1$ to $R^6$, $X^{11}$, $X^{21}$ and $X^{31}$ in the formula (77), respectively.

The Wurtz-type coupling is known as a coupling reaction between halides, and the present inventors have found how to apply this reaction to manufacture the compound of the formula (77). Examples of the halogen include fluorine, chlorine, bromine and iodine, and among them, bromine is more preferable. The reaction is conducted in the presence of, for example, an alkali metal such as metal sodium and metal lithium, a catalyst or the like. Examples of the catalyst include a copper catalyst, a nickel catalyst and a palladium catalyst, and among them, a copper catalyst is more preferable. In addition, the halide may be prepared in a state of isolation, and then coupled, alternatively, the halide may be produced in a reaction system, and then coupled (without isolation) in the same reaction system. In the present invention, specific procedures and reaction conditions of the Wurtz-type coupling are not limited particularly, but may be, for example, as described below. That is, the compounds of the formulae (78) to (80) (hereinafter, they may be simply called "diene"), potassium t-butoxide, a hexane solution of n-butyllithium, 1,2-dibromoethane, copper iodide (I) and THF as a solvent are prepared firstly, and then all of these reaction materials, the solvent and a reactor vessel are dried sufficiently. Amounts of the other materials to be used except diene and the solvent are not limited particularly, but it is more preferable to use these materials by all the same chemical equivalents so as to suppress a side reaction or the like. Next, an inside of the reactor vessel is displaced by inert gas, and t-BuOK and THF are added and solved therein. Thereafter, a temperature of the reaction system is decreased to −78° C., diene is added into the reaction system, and the hexane solution of n-BuLi is further dropped therein over the course of 2 hours. After the dropping, the temperature of the reaction system is increased to −40° C., and the reaction system is stirred further for 30 minutes. And then, after decreasing the temperature of the system to −78° C. again, 1,2-dibromoethane is added into the system, the temperature subsequently is increased to −40° C. again, and the system is stirred for 1.5 hours. Next, the temperature of the system recovers to −78° C., and then copper iodide (I) is added therein. Moreover, after stirring the system at −78° C. for 4 hours, the cooling of the system is stopped, and it is stirred further for 7 hours while the temperature thereof recovers to the room temperature gradually. Thereafter, the system is worked up by an established method so as to obtain the objective compound represented by the formula (77).

Materials to be used in this reaction, reaction temperatures, reaction time and the like are not limited to those described above, and can be set as appropriate with reference to a conventional Wurtz-type coupling reaction or the like. In addition, in the case where any of the $X^{11}$, $X^{21}$ and $X^{31}$ in the formulae (78) to (80) is an imino group, a hydrogen atom in the imino group is preferably substituted by a protecting group so as to suppress a side reaction or the like. The protecting group is not limited particularly, and known protecting groups can be used as appropriate. Examples thereof include a protecting group described in, for example, "Protective Groups in Organic Synthesis, $2^{nd}$ Edition" authored by Greene and Wuts, and specific examples include, a t-butoxycarbonyl group (Boc), an acetyl group (Ac), a benzyloxycarbonyl group (Z) and a benzyl group (Bz).

In addition, the compound of the formula (77) is a syn body, but it is generally obtained as a mixture with an anti body that is an isomer thereof. They can be separated by a generally used method such as GPC. Moreover, in the case where all of the $X^{11}$, $X^{21}$ and $X^{31}$ are not the same, many by-products are obtained besides the objective compound represented by the formula (77), and they also can be separated by the method such as column chromatography and GPC.

Furthermore, the method for manufacturing the compound of the formula (77) is not limited to the Wurtz-type coupling method, and the compound can be synthesized also by a known method. Examples of the known method include a cross-coupling method between a halide and an organometallic reagent, which is described in "Giuseppe Borsato, Ottorino De Lucchi, Fabrizio Fabris, Luca Groppo, Vittorio Lucchini, and Alfonso Zambon, J. Org. Chem., 2002, 67, p. 7894-7897." and synthesis methods described in "Harold Hart, Abdollah Bashir-Hashemi, Jihmei Luo and Mary Ann Meador, Tetrahedron, 1986, 42, p. 1641-1654.", "Harold Hart, Chung-yin Lai, Godson Chukuemeka Nwokogu and Shamouil Shamouilian, Tetrahedron, 1987, 43, p. 5203-5224." and the like. However, if using the Wurtz-type coupling method, after halogenating the compounds represented by the formulae (78) to (80), the cyclization (without isolation) also can be conducted in a reaction system that is the same as a reaction system of the halogenation, for example, as mentioned above. Thereby, the compound of the formula (77) can be synthesized from the compounds of the formulae (78) to (80) simply in one step, and thus the Wurtz-type coupling method is preferable. This is particularly effective if all of the $X^{11}$, $X^{21}$ and $X^{31}$ are methylene groups.

Then, after obtaining the compound of the formula (77), the compound of the formula (76) is obtained by the metathesis reaction of the compound of the formula (77), as mentioned above.

In addition, as a method for obtaining the compound of the formula (76) from the compound of the formula (77), for example, a below-described manufacturing method also may be used besides the metathesis method. That is, the compound represented by the formula (77) is firstly subjected to ozonolysis so as to obtain a compound represented by a below formula (77'). A condition of this ozonolysis is not limited particularly, and can be set as appropriate with reference to a known ozonolysis reaction or the like.

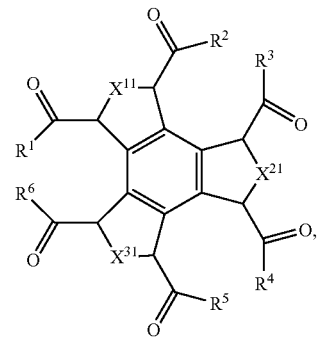

(77')

Here, in the formula, $R^1$ to $R^6$ are the same or different and each of them may be a hydrogen atom, a straight or branched alkyl group or an aromatic hydrocarbon group. $X^{11}$, $X^{21}$ and $X^{31}$ are the same or different and each of them may be a methylene group, an imino group or an oxygen atom, and in the case where any of the $X^{11}$, $X^{21}$ and $X^{31}$ is an imino group, a hydrogen atom in the imino group may be substituted by a protecting group.

The ozonolysis is known as a reaction of ozonizing a compound having a carbon-carbon unsaturated bond, and then decomposing the thus ozonized compound so as to obtain a carbonyl compound. A method for obtaining the carbonyl reaction by decomposing ozonide is, for example, a method of decomposing by water and a method of using a reductant, and more specifically is, for example, a method of reducing by $Zn-H_2O$ in the presence of acetic acid, a method of catalytic-reducing by using hydrogen in the presence of a platinum catalyst, a palladium catalyst or the like, a method of reducing by using Raney nickel, or the like. Many documents refer to ozonolysis, which are, for example, "P. S. Bailely, Chem. Rev., 1958, 58, p. 925.", "R. W. Murray, Acc. Chem. Res., 1968, 1, p. 313." and the like.

In addition, the compound represented by the formula (77') and its salt are the new compounds according to the present invention, and preferably are manufactured by a manufacturing method including ozonolysis of the compound represented by the formula (77), but may be manufactured by other methods that are not limited to this manufacturing method.

Then, after obtaining the compound represented by the formula (77'), the compound is subjected to an intramolecular coupling reaction so as to obtain the compound represented by the formula (76). A condition of this intramolecular coupling reaction is not limited particularly, and can be set as appropriate with reference to a known reaction or the like. The intramolecular coupling reaction is preferably a reductive coupling reaction using a transition metal element, and it is more preferable that the transition metal element includes titanium. Such reductive coupling of a carbonyl compound using low-valence titanium is known as a McMurry reaction. The low-valence titanium is generated usually by reducing, for example, $TiCl_3$ or a complex of $TiCl_3(DME)_{1.5}$ (DME represents dimethoxyethane) in a reaction system, and in this case, for example, Zn(Cu), $C_8K$ (potassium graphite) or the like is used as a reductant. Many documents refer to the McMurry reaction, which are, for example, "J. E. McMurry, Acc. Chem. Res., 1974, 7, p. 281.", "J. E. McMurry, Acc. Chem. Res., 1983, 16, p. 405.", "J. E. McMurry and K. L. Kees, J. Org. Chem., 1977, 42, p.2655.", "D. L. J. Clive et al., J. Am. Chem. Soc., 1988, 110, p. 6914." and the like.

After preparing the compound represented by the above chemical formula (76) as mentioned above, the compound is oxidized so as to manufacture a compound represented by a below formula (81).

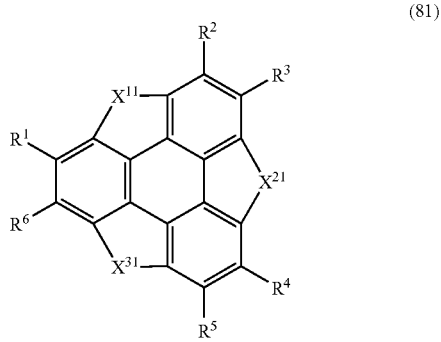

(81)

Here, $R^1$ to $R^6$, $X^{11}$, $X^{21}$ and $X^{31}$ in the formula are the same as the $R^1$ to $R^6$, $X^{11}$, $X^{21}$ and $X^{31}$ in the formula (76), respectively.

A condition of the oxidation reaction is not limited particularly, and the reaction can be caused under the same condition as that of conventional dehydrogenation. For example, an oxidizer such as DDQ and chloranil may be used, but industrially, it is preferable that a catalyst is used. The catalyst is not limited particularly, and catalysts that usually are used for dehydrogenation can be used. As the catalyst, for example, Pd—C (palladium carbon), platinum, rhodium, metal sulfur, metal selenium and the like can be used. In addition, these catalysts may be used alone or in combination of two kinds or more.

Other materials to be used and reaction conditions also are not limited particularly, and can be set as appropriate with reference to conventional dehydrogenation or the like. In the case of using the oxidizer such as DDQ or the catalyst such as Pd—C, for example, aromatic hydrocarbon such as toluene and xylene, and an ether solvent such as dioxane and dimethoxyethane can be used as a reaction solvent, and these solvents may be used alone or in combination of two kinds or more. Reaction temperatures and reaction time in this case also are not limited particularly, and can be selected as appropriate according to kinds of reaction materials or the like.

After obtaining the compound represented by the formula (81), hydrogen atoms on the $X^{11}$, $X^{21}$ and $X^{31}$ and hydrogen atoms at benzyl positions on the $R^1$ to $R^6$ are substituted as necessary so as to obtain the compound of the present invention represented by the formula (1). In the case where any of the $X^{11}$, $X_{21}$ and $X31$ is an imino group, and a hydrogen atom in the imino group is substituted by a protecting group, the imino group may be deprotected as necessary, and subsequently substituted again. A method for deprotecting is not limited particularly, and known methods may be used as appropriate according to a kind of the protecting group or the like.

A method for substituting for the hydrogen atoms on the $X^{11}$, $X^{21}$ and $X^{31}$ also is not limited particularly, and various kinds of substituents can be introduced by the same method as those of substitution reactions of diphenylmethane, fluorene, carbazole and the like that have similar chemical structures. For example, in the case where any of the $X^{11}$, $X^{21}$ and $X^{31}$ is a methylene group, in order to alkylate the methylene group, a method of detaching a hydrogen atom in the methylene group by butyllithium or the like so as to generate a carbanion, and then adding alkyl iodide or the like can be used. In addition, in order to alkoxylate, a method that is generally used for alkoxylation at a benzyl position, for example, a method of causing an alcoholysis reaction after halogenation or the like can be used. Moreover, in the case where a hydrogen atom at a benzyl position exists on any of the $R^1$ to $R^6$, a method for substituting for the hydrogen atom is not also limited particularly, and the substitution can be conducted similarly to a general substitution reaction at a benzyl position. For substituting by, for example, an alkyl group or an alkoxy group, a method similar to the above-described method and the like can be used.

According to the above-described method, the compound of the present invention represented by the formula (1) can be obtained without difficulty by the methodology of organic synthetic chemistry. However, the method for manufacturing the compound of the present invention is not limited to this, and the compound may be manufactured by any methods.

The compound of the present invention represented by the formula (1) is used suitably for an electronic material, a raw material for various kinds of fullerenes and heterofullerenes, and the like. In particular, in the case where any of the $X^1$ to $X^3$ includes a hetero atom, the compound is considered to be suitable for a synthesis raw material for heterofullerenes.

Moreover, a compound having a structure where two or more groups that are derived from a molecule of the compound represented by the formula (1) are linked via at least one of a covalent bond and a crosslinking chain (hereinafter, the compound having such a structure simply may be called a "crosslinked body" (or a "crosslinked compound")) also is included in the compounds of the present invention. Here, structures of the two or more groups may be the same or different. The crosslinking chain is not limited particularly, and may be, for example, an alkylene group, polyene or a crosslinking chain including an ester linkage, an ether linkage or the like. Among them, for example, an alkylene group is preferable, and a methylene group or a polymethylene group with the carbon number of 2 to 10 is more preferable. Moreover, it is preferable that each of the two or more groups includes at least one carbon at a benzyl position, and a binding site with the covalent bond or the crosslinking chain is the carbon at the benzyl position.

A method for manufacturing such a crosslinked body (crosslinked compound) also is not limited particularly, and known methods can be used as appropriate according to a structure or the like of the objective crosslined body, but one of the examples thereof is the following method. That is, one benzyl position of Sumanene (the compound of the formula (84)) is monohalogenated, and then is subjected to a coupling reaction with a halogenated alkylene, for example, 1,4-dibromobutane. A method for this is not particularly limited, but may be a method of adding metal Mg to the monohalogenated compound of Sumanene so as to produce a Grignard reagent, and then adding 1,4-dibromobutane so as to cause coupling. Thereby, a compound in which the benzyl positions of Sumanene are linked to each other via a tetramethylene group can be obtained. Furthermore, substituents are introduced as necessary, by the above-described method or the like, to benzyl positions that are not linked via the tetramethylene group, thus obtaining the objective crosslinked body.

In addition, in the case where the compound represented by the formula (1) and its crosslinked body have isomers such as tautomers, stereoisomers and optical isomers (enantiomers), these isomers also are included in the compound of the present invention. Moreover, in the case where the compound of the formula (1) and other compounds according to the present invention can form salts, the salts also are included in the compounds of the present invention. The salt is not limited particularly, and may be, for example, an acid addition salt or a base addition salt, furthermore, an acid for forming the acid addition salt may be an inorganic acid or an organic acid, and a base for forming the base addition salt may be an inorganic base or an organic base. The inorganic acid is not limited particularly, and examples thereof include sulfuric acid, phosphoric acid, hydrochloric acid, hydrobromic acid and hydroiodic acid. The organic acid also is not limited particularly, and examples thereof include p-toluenesulfonic acid, methanesulfonic acid, oxalic acid, p-bromobenzenesulfonic acid, carbonic acid, succinic acid, citric acid, benzoic acid and acetic acid. The inorganic base is not limited particularly, and examples thereof include ammonium hydroxide, alkali metal hydroxide, alkaline-earth metal hydroxide, carbonate and hydrogencarbonate. More specific examples include sodium hydroxide, potassium hydroxide, potassium carbonate, sodium carbonate, sodium hydrogencarbonate, potassium hydrogencarbonate, calcium hydroxide and calcium carbonate. The organic base is not limited particularly, and examples thereof include ethanolamine, triethylamine and tris(hydroxymethyl) aminomethane.

A method for manufacturing the salt of the compound of the present invention also is not limited particularly, and the salt can be manufactured by a method of, for example, adding the acid or the base described above as appropriate to the compound of the present invention by a known method.

It is preferable that, in the formula (1), the $A^1$ to $A^6$ and the substituent on the $X^1$ to $X^3$ satisfy the below-described conditions.

(Conditions of the $A^1$ to $A^6$ and the Substituent on the $X^1$ to $X^3$)

the $A^1$ to $A^6$ are the same or different, each of the $A^1$ to $A^6$ is a hydrogen atom, a straight or branched alkyl group or an aromatic hydrocarbon group, in a case where a hydrogen atom at a benzyl position exists on any of the $A^1$ to $A^6$, the hydrogen atom may be substituted by a substituent, the substituents on the $A^1$ to $A^6$ are the same or different, each of the substituents is a halogen, a low molecular-weight or a polymer chain that is straight or branched (a principal chain and a side chain of the low molecular-weight or the polymer chain may or may not include a hetero atom, may or may not include an unsaturated bond, and may or may not include a cyclic structure), a carbocyclic ring or a heterocyclic ring with the number of ring atoms of 3 to 20 (the ring may be a monocyclic ring or a condensed ring, may be saturated or unsaturated, and may or may not include a substituent), a saturated or unsaturated hydrocarbon group, a hydroxy group, an alkoxy group, an alkanoyloxy group, an alkylamino group, a dialkylamino group, an alkanoylamino group, a cyano group, a nitro group, a sulfo group, an alkyl group substituted by one or more halogens, an alkoxysulfonyl group (an alkyl group in the alkoxysulfonyl group may be substituted by one or more halogens), an alkylsulfonyl group (an alkyl group in the alkylsulfonyl group may be substituted by one or more halogens), a sulfamoyl group, an alkylsulfamoyl group, a carboxyl group, a carbamoyl group, an alkylcarbamoyl group, an alkanoyl group or an alkoxycarbonyl group, alternatively, the substituents bonded to the same $A^r$ (r is any one of integers from 1 to 6) may be bonded to each other via a covalent bond so as to form a carbocyclic ring or a heterocyclic ring with the $A^r$ to which the substituents are bonded (the ring may be a monocyclic ring or a condensed ring, may be saturated or unsaturated, and may or may not include a substituent), the substituents on the $X^1$ to $X^3$ are the same or different, in a case where the $X^a$ (a is any one of integers from 1 to 3) to which the substituent is bonded is a methylene group or a vinylidene group, each of the substituents is a halogen, a low molecular-weight or a polymer chain that is straight or branched (a principal chain and a side chain of the low molecular-weight or the polymer chain may or may not include a hetero atom, may or may not include an unsaturated bond, and may or may not include a cyclic structure), a carbocyclic ring or a heterocyclic ring with the number of ring atoms of 3 to 20 (the ring may be a monocyclic ring or a condensed ring, may be saturated or unsaturated, and may or may not include a substituent), a saturated or unsaturated hydrocarbon group, a hydroxy group, an alkoxy group, an alkanoyloxy group, an amino group, an oxyamino group, an alkylamino group, a dialkylamino group, an alkanoylamino group, a cyano group, a nitro group, a sulfo group, an alkyl group substituted by one or more halogens, an alkoxysulfonyl group (an alkyl group in the alkoxysulfonyl group may be substituted by one or more halogens), an alkylsulfonyl group (an alkyl group in the alkylsulfonyl group may be substituted by one or more halogens), a sulfamoyl group, an alkylsulfamoyl group, a carboxyl group, a carbamoyl group, an alkylcarbamoyl group, an alkanoyl group or an alkoxycarbonyl group, alternatively, the substituents bonded to the same $X^a$ (a is any one of integers from 1 to 3) may be bonded to each other via a covalent bond so as to form a carbocyclic ring or a heterocyclic ring with the $X^a$ to which the substituents are bonded (the ring may be a monocyclic ring or a condensed ring, may be saturated or unsaturated, and may or may not include a substituent), in a case where the $X^a$ to which the substituent is bonded is an iminomethylene group or an imino group, the substituent is a halogen, a low molecular-weight or a polymer chain that is straight or branched (a principal chain and a side chain of the low molecular-weight or the polymer chain may or may not include a hetero atom, may or may not include an unsaturated bond, and may or may not include a cyclic structure), a carbocyclic ring or a heterocyclic ring with the number of ring atoms of 3 to 20 (the ring may be a monocyclic ring or a condensed ring, may be saturated or unsaturated, and may or may not include a substituent), a saturated or unsaturated hydrocarbon group, a hydroxy group, an alkoxy group, an alkanoyloxy group, an alkyl group substituted by one or more halogens, a carboxyl group, a carbamoyl group, an alkylcarbamoyl group, an alkanoyl group or an alkoxycarbonyl group.

In addition, it is more preferable that, in the formula (1), the $A^1$ to $A^6$ and the substituent on the $X^1$ to $X^3$ satisfy the below-described conditions.

(Conditions of the $A^1$ to $A^6$ and the Substituent on the $X^1$ to $X^3$)

the $A^1$ to $A^6$ are the same or different, each of the $A^1$ to $A^6$ is a hydrogen atom, a straight or branched alkyl group with the carbon number of 1 to 6, a phenyl group or a naphthyl group, in a case where a hydrogen atom at a benzyl position exists on any of the $A^1$ to $A^6$, the hydrogen atom may be substituted by a substituent, the substituents on the $A^1$ to $A^6$ are the same or different, each of the substituents is a halogen, a straight or branched hydrocarbon chain that has a substituent or not and is saturated or unsaturated, a conjugated polymer chain or an oligomer chain, a carbocyclic ring or a heterocyclic ring with the number of ring atoms of 3 to 20 (the ring may be a monocyclic ring or a condensed ring, may be saturated or unsaturated, and may or may not include a substituent), a hydroxy group, a straight or branched alkyl group with the carbon number of 1 to 6, a straight or branched unsaturated hydrocarbon group with the carbon number of 2 to 6, a straight or branched alkoxy group with the carbon number of 1 to 6, a straight or branched alkanoyloxy group with the carbon number of 1 to 6, an amino group, an oxyamino group, a straight or branched alkylamino group with the carbon number of 1 to 6, a dialkylamino group (an alkyl group in the dialkylamino group is a straight or branched alkyl group with the carbon number of 1 to 6), a straight or branched alkanoylamino group with the carbon number of 1 to 6, a cyano group, a nitro group, a sulfo group, a straight or branched alkyl group with the carbon number of 1 to 6 that is substituted by one or more halogens, a straight or branched alkoxysulfonyl group with the carbon number of 1 to 6 (an alkyl group in the alkoxysulfonyl group may be substituted by one or more halogens), a straight or branched alkylsulfonyl group with the carbon number of 1 to 6 (an alkyl group in the alkylsulfonyl group may be substituted by one or more halogens), a sulfamoyl group, a straight or branched alkylsulfamoyl group with the carbon number of 1 to 6, a carboxyl group, a carbamoyl group, a straight or branched alkylcarbamoyl group with the carbon number of 1 to 6, a straight or branched alkanoyl group with the carbon number of 1 to 6 or a straight or branched alkoxycarbonyl group with the carbon number of 1 to 6, alternatively, the substituents bonded to the same $A^r$ (r is any one of integers from 1 to 6) may be bonded to each other via a covalent bond so as to form a carbocyclic ring or a heterocyclic ring with the $A^r$ to which the substituents are bonded (the ring may be a monocyclic ring or a condensed ring, may be saturated or unsaturated, and may or may not include a substituent), the substituents on the $X^1$ to $X^3$ are the same or different, in a case where the $X^a$ (a is any one of integers from 1 to 3) to which the substituent is bonded is a methylene group or a vinylidene group, the substituent is a halogen, a straight or branched hydrocarbon chain that has a substituent or not and is saturated or unsaturated, a conjugated polymer chain or an oligomer chain, a carbocyclic ring or a heterocyclic ring with the number of ring atoms of 3 to 20 (the ring may be a monocyclic ring or a condensed ring, may be saturated or unsaturated, and may or may not include a substituent), a hydroxy group, a straight or branched alkyl group with the carbon number of 1 to 6, a straight or branched unsaturated hydrocarbon group with the carbon number of 2 to 6, a straight or branched alkoxy group with the carbon number of 1 to 6, a straight or branched alkanoyloxy group with the carbon number of 1 to 6, an amino group, an oxyamino group, a straight or branched alkylamino group with the carbon number of 1 to 6, a dialkylamino group (an alkyl group in the dialkylamino group is a straight or branched alkyl group with the carbon number of 1 to 6), a straight or branched alkanoylamino group with the carbon number of 1 to 6, a cyano group, a nitro group, a sulfo group, a straight or branched alkyl group with the carbon number of 1 to 6 that is substituted by one or more halogens, a straight or branched alkoxysulfonyl group with the carbon number of 1 to 6 (an alkyl group in the alkoxysulfonyl group may be substituted by one or more halogens), a straight or branched alkylsulfonyl group with the carbon number of 1 to 6 (an alkyl group in the alkylsulfonyl group may be substituted by one or more halogens), a sulfamoyl group, a straight or branched alkylsulfamoyl group with the carbon number of 1 to 6, a carboxyl group, a carbamoyl group, a straight or branched alkylcarbamoyl group with the carbon number of 1 to 6, a straight or branched alkanoyl group with the carbon number of 1 to 6 or a straight or branched alkoxycarbonyl group with the carbon number of 1 to 6, alternatively, the substituents bonded to the same $X^a$ (a is any one of integers from 1 to 3) may be bonded to each other via a covalent bond so as to form a carbocyclic ring or a heterocyclic ring with the $X^a$ to which the substituents are bonded (the ring may be a monocyclic ring or a condensed ring, may be saturated or unsaturated, and may or may not include a substituent), in a case where the $X^a$ to which the substituent is bonded is an iminomethylene group or an imino group, the substituent is a halogen, a straight or branched hydrocarbon chain that has a substituent or not and is saturated or unsaturated, a conjugated polymer chain or an oligomer chain, a carbocyclic ring or a heterocyclic ring with the number of ring atoms of 3 to 20 (the ring may be a monocyclic ring or a condensed ring, may be saturated or unsaturated, and may or may not include a substituent), a hydroxy group, a straight or branched alkyl group with the carbon number of 1 to 6, a straight or branched unsaturated hydrocarbon group with the carbon number of 2 to 6, a straight or branched alkoxy group with the carbon number of 1 to 6, a straight or branched alkanoyloxy group with the carbon number of 1 to 6, a straight or branched alkyl group with the carbon number of 1 to 6 that is substituted by one or more halogens, a carboxyl group, a carbamoyl group, a straight or branched alkylcarbamoyl group with the carbon number of 1 to 6, a straight or branched alkanoyl group with the carbon number of 1 to 6 or a straight or branched alkoxycarbonyl group with the carbon number of 1 to 6.

Moreover, it is more preferable that, in the formula (1), the $A^1$ to $A^6$ and the substituent on the $X^1$ to $X^3$ satisfy below-described conditions.

(Conditions of the $A^1$ to $A^6$ and the Substituent on the $X^1$ to $X^3$)

the $A^1$ to $A^6$ are the same or different, each of the $A^1$ to $A^6$ is a hydrogen atom, a straight or branched alkyl group with the carbon number of 1 to 6, a phenyl group or a naphthyl group, in a case where a hydrogen atom at a benzyl position exists on any of the $A^1$ to $A^6$, the hydrogen atom may be substituted by a substituent, the substituents on the $A^1$ to $A^6$ are the same or different, each of the substituents is a halogen, a straight hydrocarbon group with the carbon number of 1 to 3000 (particularly preferably, 1 to 300, and most preferably, 1 to 30) (each bond in a principal chain of the straight hydrocarbon group may be a saturated bond or an unsaturated bond, and each hydrogen atom on the principal chain arbitrarily may be substituted by a halogen or a methyl group), a conjugated polymer chain or an oligomer chain, a cyclic substituent with a structure where any one of hydrogens is removed from any of compounds of below formulae (9) to (75) (the cyclic substituent further may be substituted by one or a plurality of substituents, the substituents may be the same or different, and each of the substituents is a halogen, a methyl group, a hydroxyl group, a methoxy group, an oxo group or an amino group),
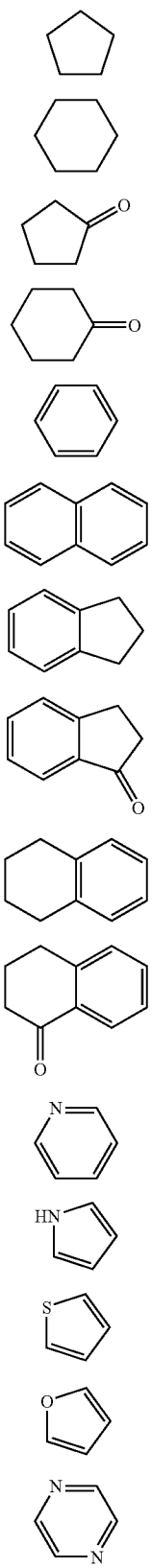
(9)
(10)
(11)
(12)
(13)
(14)
(15)
(16)
(17)
(18)
(19)
(20)
(21)
(22)
(23)
(24)
(25)
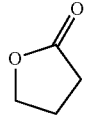
(26)
(27)
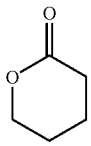
(28)
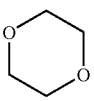
(29)
(30)
(31)
(32)
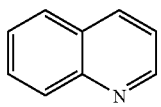
(33)
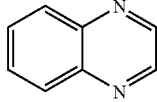
(34)
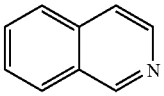
(35)
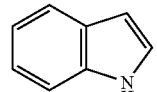
(36)
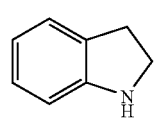
(37)

-continued
(38)
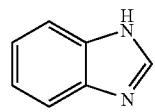
(39)
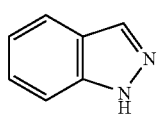
(40)
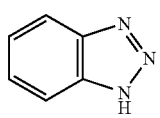
(41)
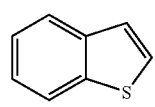
(42)
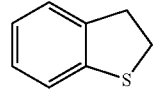
(43)
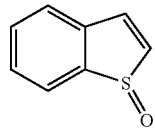
(44)
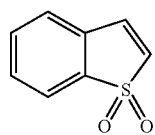
(45)
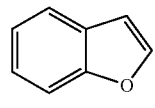
(46)
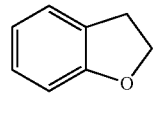
(47)
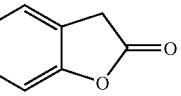
(48)
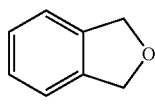
(49)
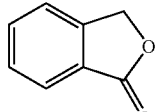
(50)
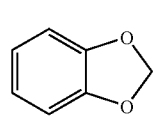
-continued
(51)
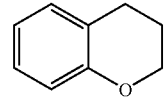
(52)
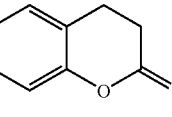
(53)
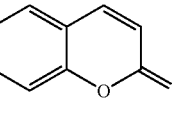
(54)
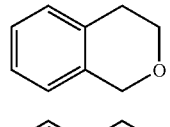
(55)
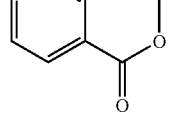
(56)
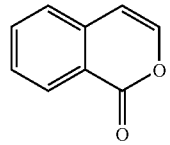
(57)
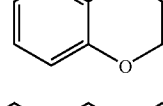
(58)
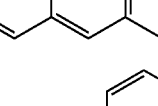
(59)
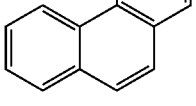
(60)
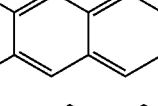
(61)
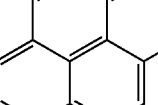
(62)
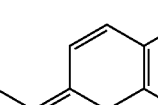

(63) 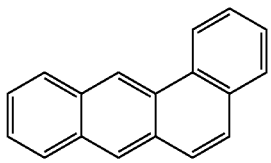

(64) 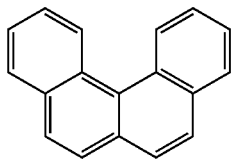

(65) 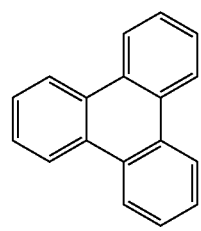

(66) 

(67) 

(68) 

(69) 

(70) 

(71) 

(72) 

(73) 

(74) 

(75) 

a hydroxy group, a straight or branched alkyl group with the carbon number of 1 to 6, a straight or branched unsaturated hydrocarbon group with the carbon number of 2 to 6, a straight or branched alkoxy group with the carbon number of 1 to 6, a straight or branched alkanoyloxy group with the carbon number of 1 to 6, an amino group, an oxyamino group, a straight or branched alkylamino group with the carbon number of 1 to 6, a dialkylamino group (an alkyl group in the dialkylamino group is a straight or branched alkyl group with the carbon number of 1 to 6), a straight or branched alkanoylamino group with the carbon number of 1 to 6, a cyano group, a nitro group, a sulfo group, a straight or branched alkyl group with the carbon number of 1 to 6 that is substituted by one or more halogens, a straight or branched alkoxysulfonyl group with the carbon number of 1 to 6 (an alkyl group in the alkoxysulfonyl group may be substituted by one or more halogens), a straight or branched alkylsulfonyl group with the carbon number of 1 to 6 (an alkyl group in the alkylsulfonyl group may be substituted by one or more halogens), a sulfamoyl group, a straight or branched alkylsulfamoyl group with the carbon number of 1 to 6, a carboxyl group, a carbamoyl group, a straight or branched alkylcarbamoyl group with the carbon number of 1 to 6, a straight or branched alkanoyl group with the carbon number of 1 to 6 or a straight or branched alkoxycarbonyl group with the carbon number of 1 to 6, alternatively, the substituents bonded to the same $A^r$ (r is any one of integers from 1 to 6) may be bonded to each other via a covalent bond so as to form a carbocyclic ring or a heterocyclic ring with the $A^r$ to which the substituents are bonded (the ring may be a monocyclic ring or a condensed ring, may be saturated or unsaturated, and may or may not include a substituent), the substituents on the $X^1$ to $X^3$ are the same or different, in a case where the $X^a$ (a is any one of integers from 1 to 3) to which the substituent is bonded is a methylene group or a vinylidene group, the substituent is a halogen, a straight hydrocarbon group with the carbon number of 1 to 3000 (particularly preferably, 1 to 300, and most preferably, 1 to 30) (each bond in a principal chain of the straight hydrocarbon group may be a saturated bond or an unsaturated bond, and each hydrogen atom on the principal chain arbitrarily may be substituted by a halogen or a methyl group), a conjugated polymer chain or an oligomer chain, a cyclic substituent with a structure where any one of hydrogens is removed from any of the compounds of the formulae (9) to (75) (the cyclic substituent further may be substituted by one or a plurality of substituents, the substituents may be the same or different, and each of the substituents is a halogen, a methyl group, a hydroxyl group, a methoxy group, an oxo group or an amino group), a hydroxy group, a straight or branched alkyl group with the carbon number of 1 to 6, a straight or branched unsaturated hydrocarbon group with the carbon number of 2 to 6, a straight or branched alkoxy group with the carbon number of 1 to 6, a straight or branched alkanoyloxy group with the carbon number of 1 to 6, an amino group, an oxyamino group, a straight or branched alkylamino group with the carbon number of 1 to 6, a dialkylamino group (an alkyl group in the dialkylamino group is a straight or branched alkyl group with the carbon number of 1 to 6), a straight or branched alkanoylamino group with the carbon number of 1 to 6, a cyano group, a nitro group, a sulfo group, a straight or branched alkyl group with the carbon number of 1 to 6 that is substituted by one or more halogens, a straight or branched alkoxysulfonyl group with the carbon number of 1 to 6 (an alkyl group in the alkoxysulfonyl group may be substituted by one or more halogens), a straight or branched alkylsulfonyl group with the carbon number of 1 to 6 (an alkyl group in the alkylsulfonyl group may be substituted by one or more halogens), a sulfamoyl group, a straight or branched alkylsulfamoyl group with the carbon number of 1 to 6, a carboxyl group, a carbamoyl group, a straight or branched alkylcarbamoyl group with the carbon number of 1 to 6, a straight or branched alkanoyl group with the carbon number of 1 to 6 or a straight or branched alkoxycarbonyl group with the carbon number of 1 to 6, alternatively, the substituents bonded to the same $X^a$ (a is any one of integers from 1 to 3) may be bonded to each other via a covalent bond so as to form a carbocyclic ring or a heterocyclic ring with the $X^a$ to which the substituents are bonded (the ring may be a monocyclic ring or a condensed ring, may be saturated or unsaturated, and may or may not include a substituent), in a case where the $X^a$ to which the substituent is bonded is an iminomethylene group or an imino group, the substituent is a halogen, a straight hydrocarbon group with the carbon number of 1 to 3000 (particularly preferably, 1 to 300, and most preferably, 1 to 30) (each bond in a principal chain of the straight hydrocarbon group may be a saturated bond or an unsaturated bond, and each hydrogen atom on the principal chain arbitrarily may be substituted by a halogen or a methyl group), a conjugated polymer chain or an oligomer chain, a cyclic substituent with a structure where any one of hydrogens is removed from any of the compounds of the formulae (9) to (75) (the cyclic substituent further may be substituted by one or a plurality of substituents, the substituents may be the same or different, and each of the substituents is a halogen, a methyl group, a hydroxyl group, a methoxy group, an oxo group or an amino group), a hydroxy group, a straight or branched alkyl group with the carbon number of 1 to 6, a straight or branched unsaturated hydrocarbon group with the carbon number of 2 to 6, a straight or branched alkoxy group with the carbon number of 1 to 6, a straight or branched alkanoyloxy group with the carbon number of 1 to 6, a straight or branched alkyl group with the carbon number of 1 to 6 that is substituted by one or more halogens, a carboxyl group, a carbamoyl group, a straight or branched alkylcarbamoyl group with the carbon number of 1 to 6, a straight or branched alkanoyl group with the carbon number of 1 to 6 or a straight or branched alkoxycarbonyl group with the carbon number of 1 to 6.

In the present invention, "halogen" means any of halogen elements, and examples thereof include fluorine, chlorine, bromine and iodine. In addition, the alkyl group is not limited particularly, and examples thereof include a methyl group, an ethyl group, a n-propyl group, an isopropyl group, a n-butyl group, an isobutyl group, a sec-butyl group and a tert-butyl group. It is also applicable to a group including an alkyl group in its structure (for example, an alkoxy group, an alkylamino group, an alkoxycarbonyl group and the like). The unsaturated hydrocarbon group is not limited particularly, and examples thereof include a vinyl group, a 1-propenyl group, an allyl group, a prop argyl group, an isopropenyl group, a 1-butenyl group, a 2-butenyl group. The alkanoyl group is not limited particularly, and examples thereof include a formyl group, an acetyl group, a propionyl group, an isobutyryl group, a valeryl group, and an isovaleryl group. It is also applicable to a group including an alkanoyl group in its structure (for example, an alkanoyloxy group, an alkanoylamino group and the like). In addition, the alkanoyl group with the carbon number of 1 means a formyl group, and it is also applicable to a group including an alkanoyl group in its structure.

It is more preferable that the conjugated polymer chain or the oligomer chain is at least one selected from the group consisting of polyphenylene, oligophenylene, polyphenylenevinylene, oligophenylenevinylene, polyene, oligovinylene, polyacetylene, oligoacetylene, polypyrrole, oligopyrrole, polythiophene, oligothiophene, polyaniline and oligoaniline (each of them may or may not be substituted by one or more substituents). In this case, it is particularly preferable that the substituent is at least one selected from the group consisting of a halogen, a methyl group, a hydroxy group, a methoxy group, an oxo group and an amino group. Moreover, it is more preferable that the conjugated polymer chain or the oligomer chain has a formula weight ranging from 30 to 30000. The formula weight ranges, particularly preferably, from 50 to 5000, and most preferably from 50 to 1000.

Moreover, in the formula (1), in a case where the substituents bonded to the same $A^r$ (r is any one of integers from 1 to 6) or the same $X^a$ (a is any one of integers from 1 to 3) are bonded to each other via a covalent bond so as to form a carbocyclic ring or a heterocyclic ring with the $A^r$ or the $X^a$ to which the substituents are bonded (the ring may be a monocyclic ring or a condensed ring, may be saturated or unsaturated, and may or may not include a substituent), the number of ring atoms of the ring ranges from 3 to 20, and the substituent is at least one selected from the group consisting of a halogen, a methyl group, a hydroxy group, a methoxy group, an oxo group and an amino group.

In addition, in the formula (1), in a case where at least one of the substituents on the $X^1$ to $X^3$ is combined with the $X^a$ to which the substituent is bonded and a benzene nucleus to which the $X^a$ further is bonded so as to form a conjugated system, the compound can be used for an electronic material or the like more preferably. Various kinds of such compounds exist, and examples thereof include compounds represented by below formulae (89) to (91). However, these compounds of the formulae (89) to (91) are just examples, and the above-described compound is not limited to them.

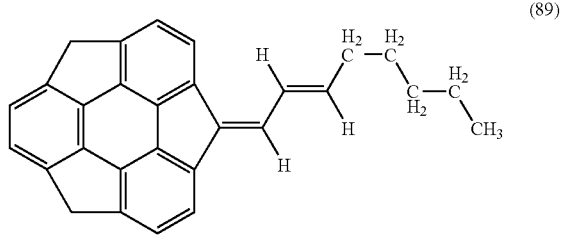

(89)

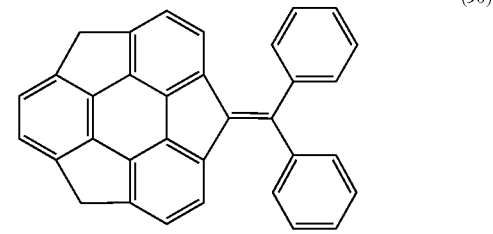

(90)

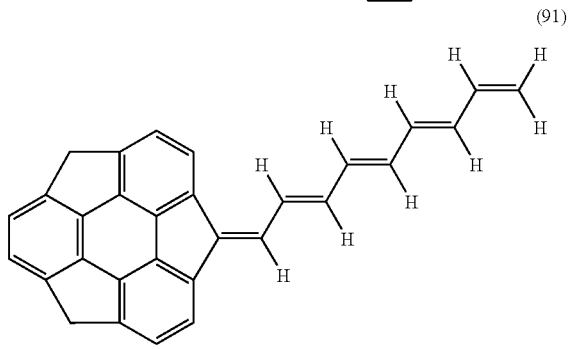

(91)

In the formula (1), a compound in which no substituent exists on the $X^1$ to $X^3$ (that is, none of the hydrogen atoms on the $X^1$ to $X^3$ is substituted by the substituent) can be used as, for example, a synthesis raw material and the like for other derivatives.

It may be preferable for the compound that all of the $A^1$ to $A^6$ are hydrogen atoms for its convenient use as a synthesis raw material and the like, but if the $A^1$ to $A^6$ include an alkyl group or an aromatic hydrocarbon group, the compound preferably can be used for a synthesis of the corresponding derivative or the like.

In addition, it is preferable that, in the formula (1), each of the $X^1$ to $X^3$ is, for example, at least one selected from the group consisting of a methylene group, a vinylidene group, an imino group and an oxygen atom, and it is more preferable that all of the $X^1$ to $X^3$ are methylene groups. In particular, a compound in which all of the $A^1$ to $A^6$ are hydrogen atoms, all of the $X^1$ to $X^3$ are methylene groups, and none of them is substituted, that is, Sumanene as a parent compound, is conveniently used as a synthesis raw material and the like for various kinds of derivatives.

Moreover, the complex of the present invention includes a complexation structure of the compound of the present invention represented by the formula (1) or its crosslinked body and a metal element, and the compound of the formula (1) or its crosslinked body may be a tautomer or a stereoisomer thereof. The complex of the present invention or its salt preferably can be used as, for example, a photosensitizer, a catalyst and the like, but its use is not limited to these. In the case of use as a catalyst, a polymerization catalyst is more preferable. The metal element may include one kind of metal element or a combination of two kinds or more, but preferably include a transition metal element. More preferably, the transition metal element includes at least one selected from the group consisting of yttrium (Y), samarium (Sm), titanium (Ti), zirconium (Zr), hafnium (Hf), vanadium (V), niobium (Nb), tantalum (Ta), chrome (Cr), molybdenum (Mo), manganese (Mn), rhenium (Re), iron (Fe), ruthenium (Ru), iridium (Ir), cobalt (Co), rhodium (Rh), tungsten (W), nickel (Ni), palladium (Pd), platinum (Pt) and osmium (Os).

Each of the photosensitizer and the catalyst of the present invention includes the complex of the present invention or a salt of the complex, and the electronic material of the present invention includes the compound of the present invention, a tautomer of the compound or a stereoisomer of the compound, or a salt of any of the compound, the tautomer and the stereoisomer, whereby the photosensitizer, the catalyst and the electronic material respectively show excellent performances.

EXAMPLE

Examples of the present invention will be described below.

(Measurement Conditions etc.)

Nuclear magnetic resonance (NMR) spectra were measured by using a device with a trade name of Mercury300 (at 300 MHz during measurement of $^1$H) manufactured by Varian Inc. Chemical shifts are shown in parts per million (ppm). Tetramethylsilane (TMS) was used for an internal standard of 0 ppm. A coupling constant (J) is shown in hertz, and codes of s, d, t, q, m and br denote a singlet, a doublet, a triplet, a quartet, a multiplet and a broad line, respectively. High-resolution mass spectroscopy (HRMS) was conducted by an electron impact method or a chemical ionization method, using JMS-DX-303 (trade name) manufactured by JEOL. Ultraviolet and visible absorption spectra and emission spectra (UV-VIS) were measured by using U-3500 (trade name) manufactured by Hitachi, Ltd. Measurement values (wavelengths) of these spectra are shown in nm. Infrared absorption spectra (IR) were measured by a KBr method using FT/IR 480 plus (trade name) manufactured by JASCO Corporation. Measurement values (wave numbers) of the spectra are shown in cm$^{-1}$, and codes of m and w denote medium and weak, respectively. Melting points were measured by using Yanagimoto MicroPoint Apparatus (trade name) manufactured by YANAGIMOTO SEISAKUSHO: KK. For column-chromatographic separation, silica gel (trade name: Wakogel CF-200, manufactured by Wako Pure Chemical Industries, Ltd.) was used. As plates for thin layer chromatography (TLC), Wakogel BF-5 (trade name) manufactured by Wako Pure Chemical Industries, Ltd. was used. GPC was conducted by using LC-908 (trade name) manufactured by JASCO Corporation. All of chemical materials are in reagent grades. Norbornadiene was purchased from Tokyo Kasei Kogyo Co., Ltd. (at a price of 16000 yen per 500 mL). A hexane solution of n-BuLi was purchased from KANTO KAGAKU; (PCy$_3$)$_2$RuCl$_2$=CHPh, from Aldrich Corp.; ethylene, from OSAKA OXYGEN IND LTD; t-BuOK, 1,2-dibromoethane, copper iodide (I), toluene and DDQ, from Wako Pure Chemical Industries, Ltd, respectively.

(Synthesis of Sumanene)

Sumanene was synthesized according to the above-described Scheme 1. The Scheme 1 will be described below again.

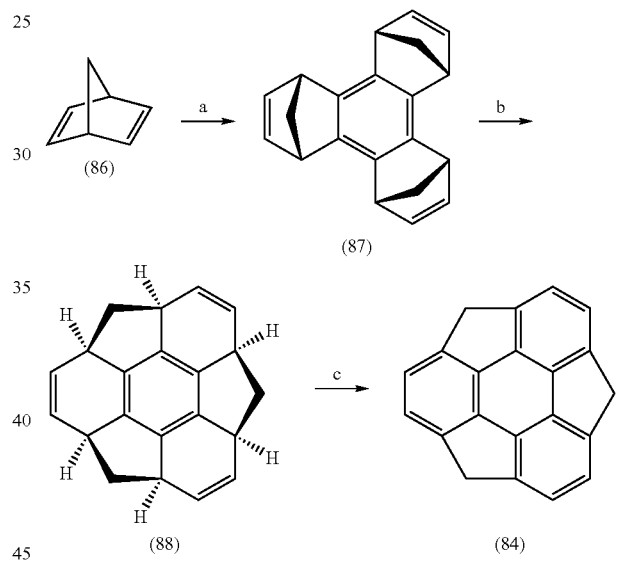

Scheme 1

Condition of the Reaction
a) BuLi, t-BuOK, BrCH$_2$CH$_2$Br, THF, −78° C. to −45° C. subsequently CuI, room temperature
b) catalyst quantity of (PCy$_3$)$_2$RuCl$_2$=CHPh, CH$_2$=CH$_2$, toluene, 0° C. to 80° C.
c) DDQ, toluene, 110° C.

Specific procedures, processes and the like will be described below.

[Step a: Synthesis of syn-benzotris(norbornadiene) (the Above Formula (87))]

First, a three-necked flask of 1 L was subjected to vacuum and dried by heat, and subsequently, its volume was displaced with argon. Then, t-BuOK (120 mmol, 13.5 g) and 180 mL of dehydrated THF were added into the flask, and were stirred. Next, a temperature of the reaction system was decreased to −78° C., and while the reaction system was kept stirred, norbornadiene (2,5-norbornadiene, 240 mmol, 22.1 g) represented by the formula (86) was added therein, and subsequently, a hexane solution of n-BuLi (concentration: 1.56 mol/L, equivalent to 120 mmol of n-BuLi) was dropped therein over the course of 2 hours. After the dropping, the temperature of the reaction system was increased to −40° C., and the reaction system further was stirred for 30 minutes. Then, after decreasing the temperature of the system to −78° C. again, 1,2-dibromoethane (60 mmol, 11.3 g) was added into the system, the temperature subsequently was increased to −40° C. again, and the system was stirred for 1.5 hours. Next, the temperature of the system recovered to −78° C., and then copper iodide (I) (120 mmol, 22.9 g) was added therein. Moreover, after stirring the system at −78° C. for 4 hours, the cooling of the system was stopped, and it was further stirred for 7 hours while the temperature thereof recovered to the room temperature gradually. Thereafter, the reaction was inhibited by using a saturated aqueous solution of ammonium chloride, and it was subjected to sellite filtration. The thus obtained filtrate was extracted with ether, and a residual water layer further was extracted sufficiently with ether, and an organic layer obtained by mixing these ether solutions was washed with water, and then was dried by $MgSO_4$. Subsequently, after evaporating the solvent under a reduced pressure, residues were separated by silica gel column chromatography (hexane:dichloromethane=4:1), thereby obtaining a diastereoisomeric mixture of syn-benzotris(norbornadiene) and anti-benzotris(norbornadiene). Moreover, the mixture was separated by GPC so as to obtain syn-benzotris(norbornadiene) (yield: 108 mg, isolation yield: 2%) as an objective compound and anti-benzotris(norbornadiene) (yield: 270 mg, isolation yield: 5%) separately. Physical properties of these compounds will be described below.

Syn-benzotris(norbornadiene): HRMS: 270.1403, melting point: 195° C. (dec), $^1$H-NMR (300 MHz, $CDCl_3$): δ=6.57 (t, J=1.8 Hz, 6 H), 3.90-3.87 (m, 6 H), 2.22 (dt, J=7.2, 1.5 Hz, 3 H), 2.08 (dt, J=7.2, 1.5 Hz, 3 H);

$^{13}$C-NMR (75 MHz, $CDCl_3$): 141.59, 137.66, 66.73, 17.44 ppm.

Anti-benzotris(norbornadiene): $^1$H-NMR (300 MHz, $CDCl_3$): δ=6.68 (t, J=1.8 Hz, 2 H), 6.65 (dd, J=5.4, 3.0 Hz, 2 H), 6.59 (dd, J=5.4, 3.0 Hz, 2 H), 3.90-3.87 (m, 2 H), 3.87-3.85 (m, 4 H), 2.05 (dt, J=7.2, 1.5 Hz, 4 H), 2.00(dt, J=7.2, 1.5 Hz, 4 H).

[Step b: Synthesis of Hexahydrosumanene (the Above Formula (88))]

First, a three-necked flask of 200 mL was subjected to vacuum and dried by heat, and subsequently, its volume was displaced with argon. A solution obtained by solving syn-benzotris(norbornadiene) (0.074 mmol, 20 mg) into 100 mL of toluene was added into the flask. Next, the temperature of the system was decreased to −78° C., and ethylene gas was introduced into the system sufficiently by bubbling so as to let the system be in an ethylene atmosphere. Thereafter, the temperature of the system recovered to a room temperature, $(PCy_3)_2RuCl_2$=CHPh (0.0037 mmol, 3 mg, 5 mol %) was added to the system, and the system was stirred at the room temperature for 24 hours while maintaining the ethylene atmosphere. Moreover, after the system was kept in an argon atmosphere and was refluxed by heat for 48 hours, the obtained reaction mixture was filtrated by silica gel. From this filtrate, the solvent therein was evaporated under a reduced pressure. The thus obtained crude product was isolated by thin layer chromatography (hexane:toluene=5:1), and finally was purified by GPC, thereby obtaining hexahydrosumanene (yield: 4 mg, isolation yield: 20%) as an objective compound. Physical properties of this compound will be described below.

HRMS: Found: m/z=270.1412, Calcd for $C_{21}H_{18}$: M=270.1408, melting point: 180° C. (dec), $^1$H-NMR(300 MHz, $CDCl_3$): δ=5.69 (s, 6 H), 3.81 (dd, 6 H, J=9.9 and 7.2 Hz), 2.78 (dt, 3 H, J=11.4 and 7.2 Hz), 1.01 (dt, 3 H, J=9.9 and 11.4 Hz); $^{13}$C-NMR (75 MHz, $CDCl_3$): 141.91, 129.28, 43.66, 40.35 ppm., IR(KBr): ν=3010(m), 2919(m), 2814(m), 1595(w), 1445(w), 1260(w) $cm^{-1}$, UV-VIS($CH_2Cl_2$): maximum absorption wavelength (Absorption $λ_{max}$)=240 nm, maximum emission wavelength (Emission $λ_{max}$)=331 nm (excitation wavelength (Excitation λ)=240 nm).

[Step c: Synthesis of Sumanene (the Above Formula (84))]

Figure 2:
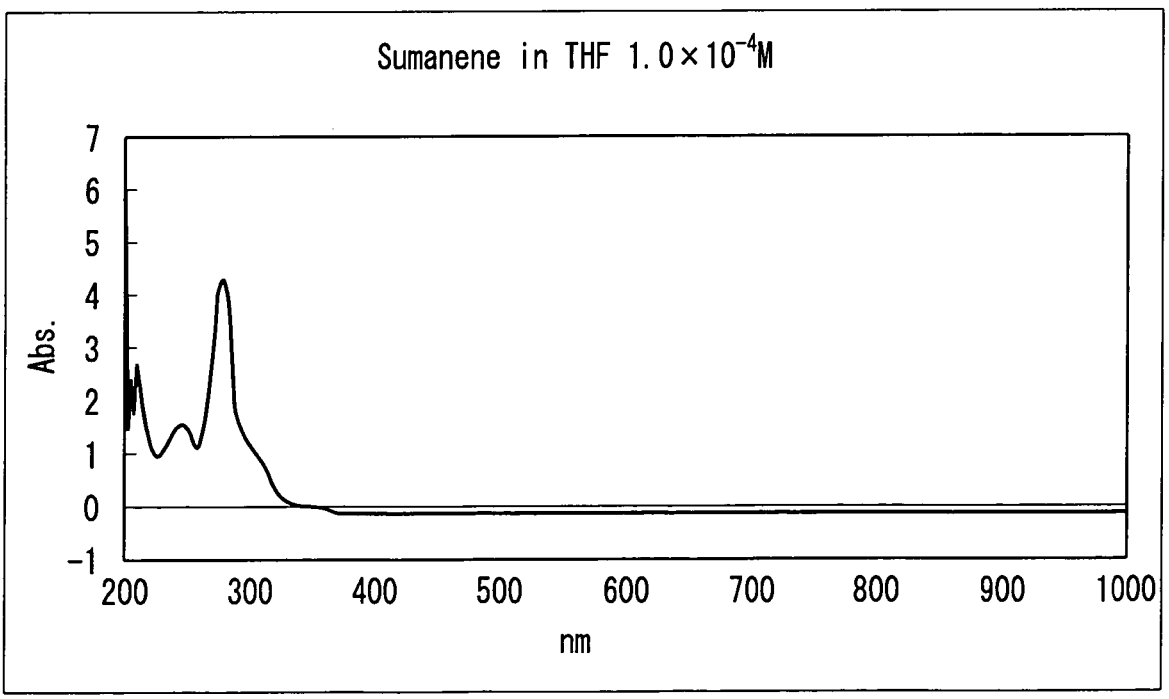
FIG. 2 is an UV-VIS spectrogram of Sumanene, where THF is used as a solvent.
Figure 3:
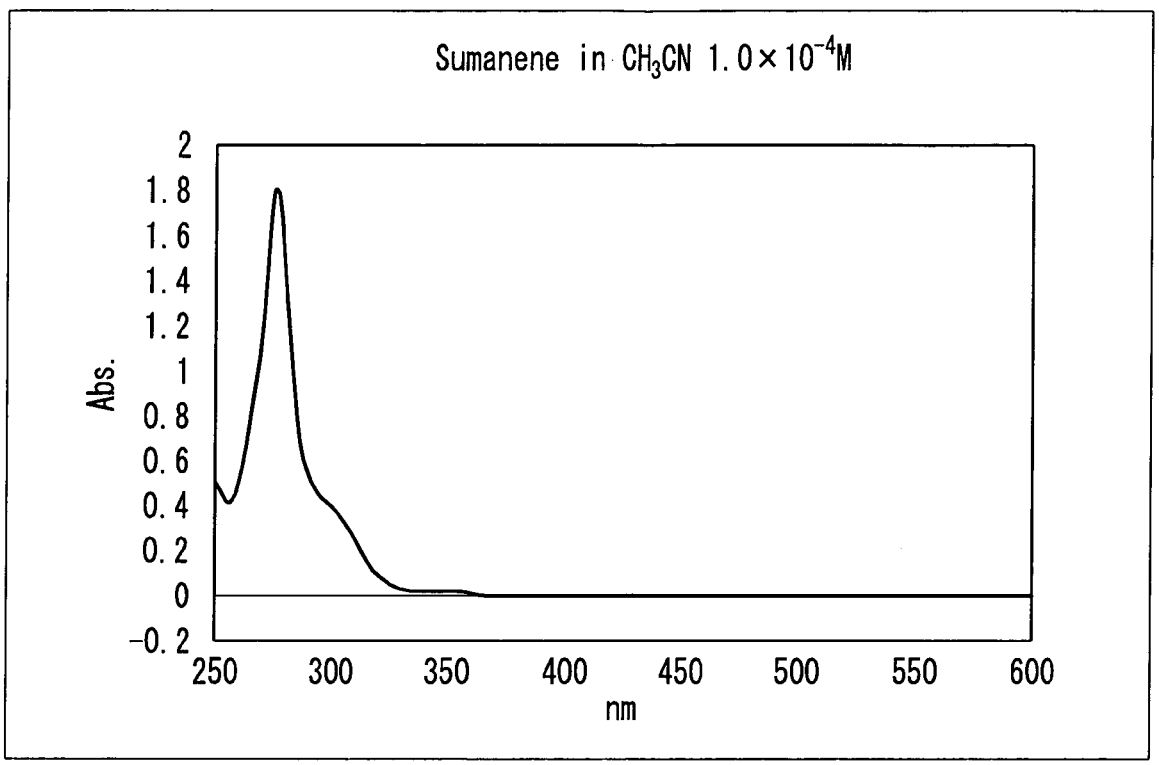
FIG. 3 is an UV-VIS spectrogram of Sumanene, where $CH_3CN$ is used as a solvent.
Figure 4:
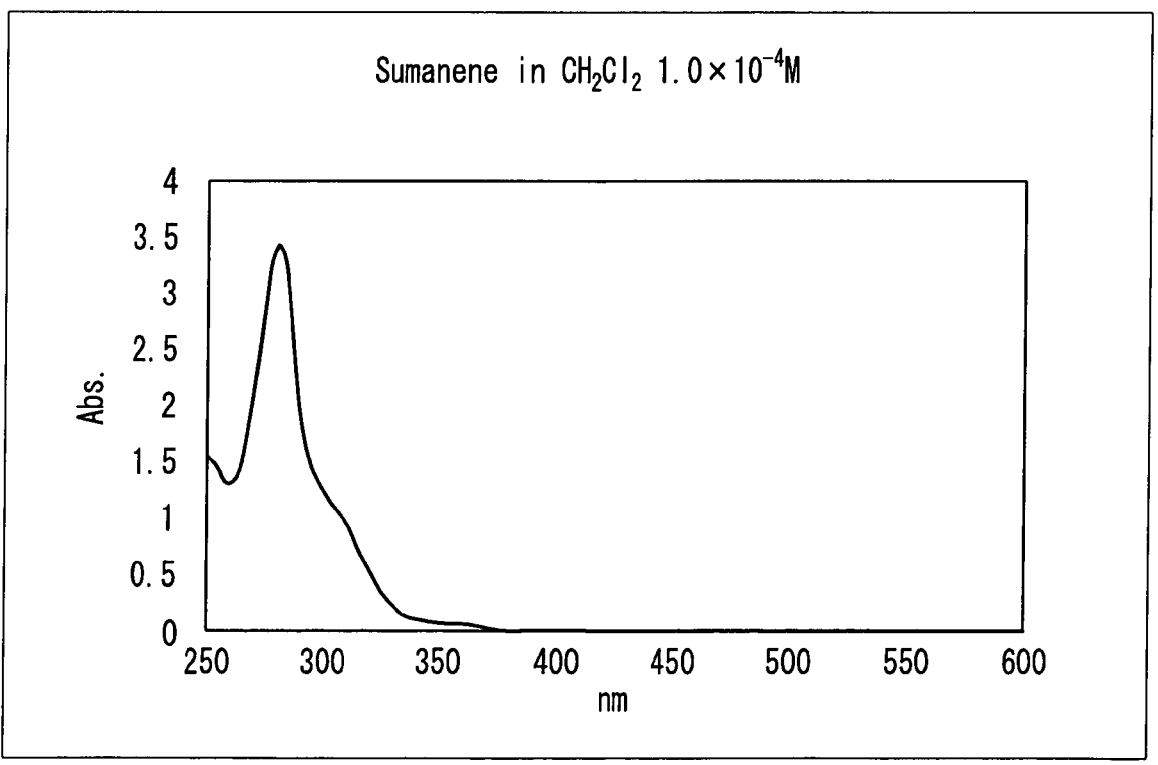
FIG. 4 is an UV-VIS spectrogram of Sumanene, where $CH_2Cl_2$ is used as a solvent.
Figure 5:
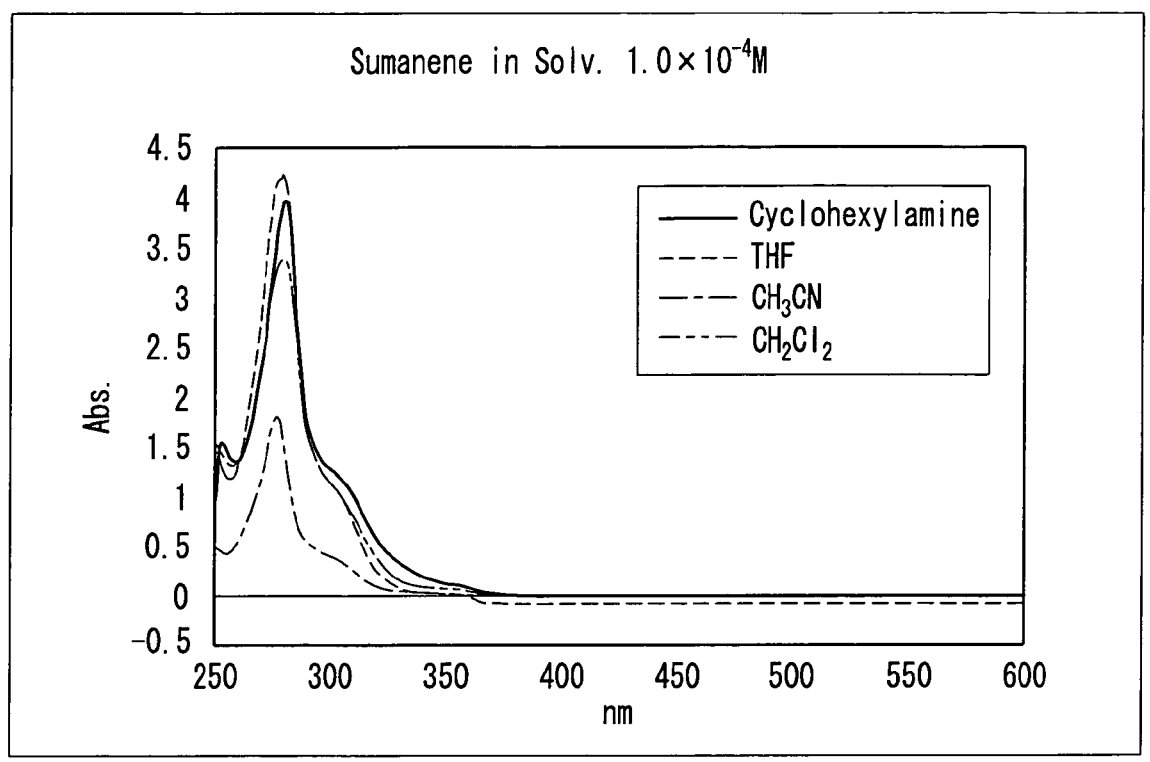
FIG. 5 is an view showing all of the spectrograms of FIGS. 1 to 4 in one.

First, a double-necked flask of 10 mL was subjected to vacuum and dried by heat, and subsequently, its volume was displaced with argon. Next, a solution obtained by solving hexahydrosumanene (0.011 mmol, 3 mg) into 2 mL of toluene was added into the flask by using a syringe, and DDQ (0.0385 mmol, 9 mg) further was added therein, and subsequently, the system was heated at 110° C. for 20 hours. After the reaction, the solvent was evaporated under a reduced pressure, and residues were separated by thin layer chromatography (hexane), thereby obtaining Sumanene (yield: 2 mg, isolation yield: 67%) as an objective compound. Physical properties of this compound will be described below. In addition, UV-VIS absorption spectrograms of this compound will be shown in FIGS. 1 to 5. Used solvents are cyclohexylamine (CHA) in FIG. 1, tetrahydrofuran (THF) in FIG. 2, acetonitrile ($CH_3CN$) in FIG. 3 and dichloromethane ($CH_2Cl_2$) in FIG. 4, where concentrations of all the solutions are $1.0×10^{-4}$ M. Moreover, FIG. 5 is a view showing all of the spectrograms of FIGS. 1 to 4 in one.

HRMS: Found: m/z=264.0923, Calcd for $C_{21}H_{12}$: M=264.0939, melting point: 115° C., $^1$H-NMR(300 MHz, $CDCl_3$): δ=7.01 (s, 6 H), 4.71 (d, J=19.5 Hz, 3 H), 3.42 (d, J=19.5 Hz, 3 H); $^{13}$C-NMR (75 MHz, $CDCl_3$): 148.78, 148.60, 123.15, 41.77 ppm., IR(KBr): ν=2950(m), 2922(m), 1653(m), 1558(m) $cm^{-1}$, UV-VIS (cyclohexylamine (CHA), $1.0×10^{-4}$ M): maximum absorption wavelength (Absorption $λ_{max}$)=279 nm(log ε=4.56), UV-VIS(tetrahydrofuran (THF), $1.0×10^{-4}$ M): maximum absorption wavelength (Absorption $λ_{max}$)=278 nm (log ε=4.62), UV-VIS (acetonitrile ($CH_3CN$), $1.0×10^{-4}$ M): maximum absorption wavelength (Absorption $λ_{max}$)=276 nm (log ε=4.25), UV-VIS($CH_2Cl_2$): maximum absorption wavelength (Absorption $λ_{max}$)=278 nm (log ε=4.52), maximum emission wavelength (Emission $λ_{max}$)= 376 nm (excitation wavelength (Excitation λ)=278 nm). In addition, when temperature-variable $^1$H-NMR (300 MHz, $d_{10}$-p-xylene) was measured at a temperature ranging from 25° C. to 140° C., a critical temperature Tc was 140° C. or more, inversion energy $ΔG^‡$ was 19.4 kcal/mol or more which was calculated from the Tc, the chemical shift value and the coupling constant J.

As mentioned above, according to the manufacturing method of the present invention, Sumanene can be synthesized in only three steps from norbornadiene that can be obtained easily at low cost. In addition, since all of the steps proceed under relatively moderate conditions, this manufacturing method enables easy industrial processing and a mass-synthesis of Sumanene by a method, for example, using a dehydrogenation catalyst instead of DDQ or the like.

INDUSTRIAL APPLICABILITY

As described above, the present invention can provide Sumanene, its derivative and a method for manufacturing Sumanene and its derivative. According to the manufacturing method of the present invention, Sumanene can be mass-synthesized under a moderate condition. Moreover, fullerenes that conventionally are difficult to obtain, unknown fullerenes, heterofullerenes and the like also can be synthesized by using Sumanene or its derivative of the present invention as a synthesis raw material, and thus it can be expected that possibilities of designing new materials will be highly enhanced. Furthermore, the compound of the present invention has a high value as a synthesis raw material, and besides, the compound itself has a high value as a material for basic research on industrial materials such as electronic materials, model compounds such as metal-inclusion type fullerene compounds and the like. That is, the compound of the present invention can be applied to most of the fields of electronic materials in which the applications of fullerenes and carbon nanotubes are currently expected, and thus its wide use in both of the basic technology and the applied technology is expected. Furthermore, since it is expected that the compound of the present invention can be applied to a photosensitizer, a polymerization catalyst and the like by, for example, being complexed with a transition metal or the like, its value in industrial applicability is tremendous.

The invention claimed is:

1. A compound represented by a below-described general formula (1), a tautomer of the compound, a stereoisomer of the compound, or a salt of any of the compound, the tautomer and the stereoisomer,

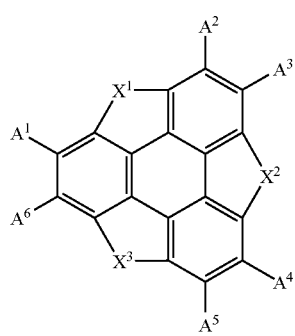

(1)

where, in the formula (1), all of the $A^1$ to $A^6$ are hydrogen atoms, $X^1$ to $X^3$ are the same or different, and each of the $X^1$ to $X^3$ may be a methylene group (a below formula (2)) or a vinylidene group (a below formula (3)), in a case where a hydrogen atom exists on any of the $X^1$ to $X^3$, the hydrogen atom may be substituted by a substituent,

(2)

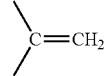

(3)

the substituents on the $X^1$ to $X^3$ are the same or different, and each of the substituents on the $X^1$ to $X^3$ is a straight or branched chain that has a substituent and is saturated or unsaturated, a carbocyclic ring with the number of ring atoms of 3 to 20 (the ring may be a monocyclic ring or a condensed ring, may be saturated or unsaturated, and may or may not comprise a substituent), a hydroxy group or a straight or branched unsaturated hydrocarbon group with the carbon number of 2 to 6.

2. The compound, the tautomer or the compound, the stereoisomer of the compound, or the salt of any of the compound, the tautomer and the stereoisomer according to claim 1, wherein, in the formula (1), each of the $X^1$ to $X^3$ is unsubstituted.

3. The compound, the tautomer of the compound, the stereoisomer of the compound, or the salt of any of the compound, the tautomer and the stereoisomer according to claim 1, wherein each of the $X^1$ to $X^3$ is tbe methylene group having the formula (2).

4. A compound represented by a below formula (76) or a salt of the compound,

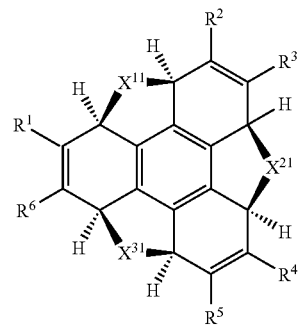

(76)

where, in the formula, $R^1$ to $R^6$ are the same or different, each of the $R^1$ to $R^6$ is a hydrogen atom or an aromatic hydrocarbon group, $X^{11}$, $X^{21}$ and $X^{31}$ are the same or different, each of the $X^{11}$, $X^{21}$ and $X^{31}$ is a methylene group.

5. The compound or the salt of the compound according to claim 4, wherein the $R^1$ to $R^6$ are the same or different, and each of the $R^1$ to $R^6$ is a hydrogen atom or a phenyl group.

* * * * *